US010322255B2

(12) United States Patent
Wells et al.

(10) Patent No.: US 10,322,255 B2
(45) Date of Patent: Jun. 18, 2019

(54) NEBULIZE ADAPTER KIT

(71) Applicants: Bobby Wells, Los Angeles, CA (US); Dolores Harge, Los Angeles, CA (US)

(72) Inventors: Bobby Wells, Los Angeles, CA (US); Dolores Harge, Los Angeles, CA (US)

( * ) Notice: Subject to any disclaimer, the term of this patent is extended or adjusted under 35 U.S.C. 154(b) by 0 days.

(21) Appl. No.: 15/277,279

(22) Filed: Sep. 27, 2016

(65) Prior Publication Data

US 2018/0085546 A1 Mar. 29, 2018

(51) Int. Cl.

*A61M 16/08* (2006.01)
*A61M 16/14* (2006.01)
*A61M 16/20* (2006.01)

(52) U.S. Cl.

CPC .... *A61M 16/0833* (2014.02); *A61M 16/0808* (2013.01); *A61M 16/0875* (2013.01); *A61M 16/14* (2013.01); *A61M 16/201* (2014.02)

(58) Field of Classification Search

CPC ............ A61M 16/0833; A61M 16/201; A61M 16/0808; A61M 16/0875; A61M 16/14
See application file for complete search history.

(56) References Cited

U.S. PATENT DOCUMENTS

| | | | | |
|---|---|---|---|---|
| 4,150,071 | A * | 4/1979 | Pecina | A61M 15/00 128/200.11 |
| 4,253,468 | A * | 3/1981 | Lehmbeck | A61B 5/09 128/200.18 |
| 4,396,015 | A * | 8/1983 | Johnson | A61M 15/0018 128/200.14 |
| D294,175 | S | 2/1988 | Briggs | |
| 4,951,661 | A | 8/1990 | Sladek | |
| 5,062,419 | A * | 11/1991 | Rider | A61M 16/16 128/200.14 |
| 5,396,883 | A | 3/1995 | Knupp et al. | |
| D431,634 | S | 10/2000 | Mantz | |
| 6,328,030 | B1 | 12/2001 | Kidwell et al. | |
| 6,725,858 | B2 | 4/2004 | Loescher | |
| 2007/0101994 | A1* | 5/2007 | Waters | A61M 11/06 128/205.12 |
| 2008/0115787 | A1* | 5/2008 | Ingenito | A61M 16/12 128/205.13 |
| 2011/0114091 | A1 | 5/2011 | Lee et al. | |
| 2014/0137860 | A1 | 5/2014 | Lanier | |

* cited by examiner

*Primary Examiner* — Gregory A Anderson
*Assistant Examiner* — Jonathan S Paciorek

(57) ABSTRACT

A nebulizer adapter kit including a T-shaped adapter having cylindrical upper and lower portions and a safety cap on the lower portion. A direct flow valve on and in fluid communication with each of the proximal end and a channel stemming from a nebulizer medicine reservoir separate from the nebulizer machine. The direct flow valve is in operational and fluid communication with a direct flow tube. A shut-off valve is between and in fluid communication with the direct flow tube and a mouthpiece. A drip-reduction ring on the adapter bottom end inserts within an upper outlet of the nebulizer machine. A gas source is attachable to and in fluid communication with the nebulizer machine to convert liquid therapy medication into a mist, which is formed within the direct flow valve, rather than inside the nebulizer machine.

1 Claim, 5 Drawing Sheets

NEBULIZE ADAPTER KIT

CROSS-REFERENCE TO RELATED APPLICATIONS

Not Applicable

FEDERALLY SPONSORED RESEARCH OR DEVELOPMENT

Not Applicable

INCORPORATION BY REFERENCE OF MATERIAL SUBMITTED ON A COMPACT DISK

Not Applicable

BACKGROUND OF THE INVENTION

Various types of connectors and adapters used to fluidly connect a nebulizer to another device, such as a fluid collection reservoir, an gas therapy tank, a ventilator, or a respirator, are known in the prior art. However, what is needed is a nebulizer adapter kit including a T-shaped adapter to which a plurality of attachment pieces, including a mouthpiece, a shut-off valve directly adjacent and in fluid communication with the mouthpiece which controls the passage of a mist of liquid therapy medication therethrough into the mouthpiece from a direct flow tube. The direct flow tube is disposed within a channel of a nebulizer medicine reservoir and has an upper end and a lower end. The upper end is attached to and in fluid communication direct flow valve on a proximal end of a T-shaped adapter. The lower end of the direct flow tube is attached directly to and is in fluid communication with a nebulizer medicine reservoir, which is separate from the nebulizer machine. A safety cap is disposed on an opposite end of the T-shaped adapter from the direct flow tube. On a lower portion of the T-shaped adapter is a drip-reduction ring which is disposed within an upper outlet of a nebulizer. An amount of liquid therapy medication is disposed within the nebulizer medicine reservoir. A gas source is in fluid communication with the nebulizer machine to transform the liquid therapy medication into a mist within the direct flow tube when the direct flow valve is in an open condition and the safety cap is attached to the T-shaped adapter. When the shut-off valve is open, the mist is directed through the mouthpiece.

FIELD OF THE INVENTION

The present invention relates to nebulizer connectors and adapters to connect a nebulizer to another device, and more particularly, to a nebulizer adapter kit including a an adapter tee and a plurality of attachment pieces attachable to the adapter tee.

SUMMARY OF THE INVENTION

The general purpose of the present nebulizer adapter kit, described subsequently in greater detail, is to provide a nebulizer adapter kit which has many novel features that result in a nebulizer adapter kit which is not anticipated, rendered obvious, suggested, or even implied by prior art, either alone or in combination thereof.

To accomplish this, the present nebulizer adapter kit includes a T-shaped adapter having a cylindrical upper portion and a cylindrical lower portion centrally disposed in a position perpendicular to and in fluid communication with the upper portion. The upper portion has a proximal end and a distal end. The upper portion has a safety cap disposed on the distal end. The lower portion has a bottom end and a top end.

A direct flow valve is disposed on and in fluid communication with the proximal end of the T-shaped adapter upper portion. The direct flow valve has an open position and an alternate closed position.

A direct flow tube, shown best in FIG. 2, is disposed within a channel of and in direct fluid communication with a nebulizer medicine reservoir. The direct flow tube has an upper end and a lower end. The direct flow valve is in operational communication and in fluid communication with the direct flow tube lower end. The nebulizer medicine reservoir is a separate body from and in indirect fluid communication with a nebulizer machine. An amount of liquid therapy medication is disposed within the nebulizer medicine reservoir.

A shut-off valve is disposed between and in fluid communication with the upper end of the direct flow tube and a mouthpiece. The shut-off valve has an open position and an alternate closed position. A drip-reduction ring is disposed on the bottom end of the T-shaped adapter lower portion. The drip-reduction ring is insertable within an upper outlet of the nebulizer machine. The drip-reduction ring is provided to prevent backflow into the nebulizer machine. A gas source is attachable to and configured to be in fluid communication with the nebulizer machine.

Upon activation of the nebulizer machine, the attachment of the gas source to the nebulizer machine, the positioning of the shut-off valve in the open position, the positioning of the direct flow valve in the open position, the gas source is configured to transform the liquid therapy medication disposed within the nebulizer medicine reservoir into a mist. Upon transformation of the liquid therapy medication into a mist, the mist is directed into the direct flow tube, through the open shut-off valve, and through the mouthpiece for inhalation by the user.

Thus has been broadly outlined the more important features of the present nebulizer adapter kit so that the detailed description thereof that follows may be better understood and in order that the present contribution to the art may be better appreciated.

BRIEF DESCRIPTION OF THE DRAWINGS

Figures

DETAILED DESCRIPTION OF THE DRAWINGS

Figure 1:
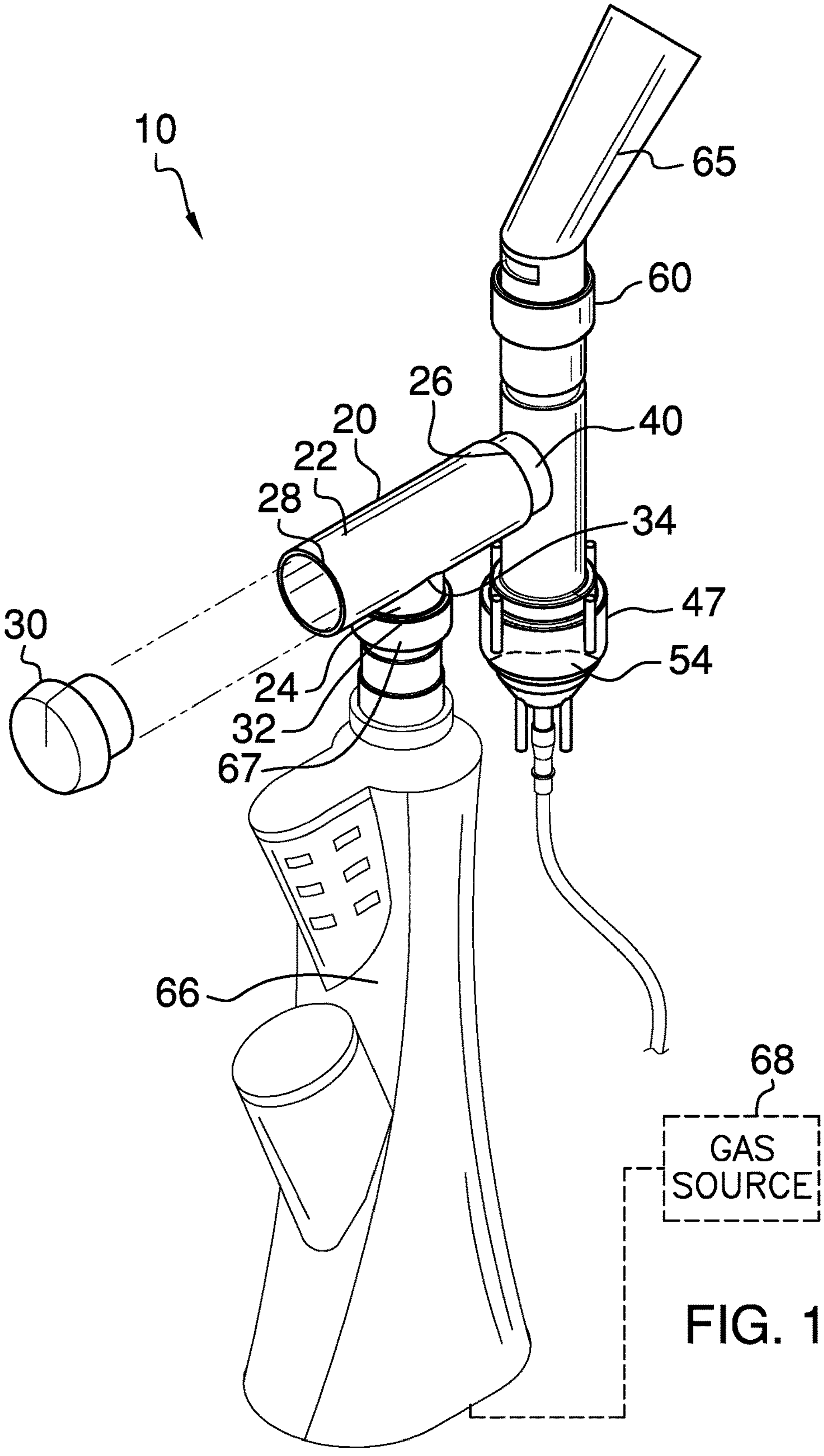
FIG. 1 is an isometric view.

With reference now to the drawings, and in particular FIGS. 1 through 5 thereof, an example of the instant nebulizer adapter kit employing the principles and concepts of the present nebulizer adapter kit and generally designated by the reference number 10 will be described.

Referring to FIGS. 1 through 5, the present nebulizer adapter kit 10 is illustrated. The nebulizer adapter kit 10 includes a T-shaped adapter 20 having a cylindrical upper portion 22 and a cylindrical lower portion 24 centrally disposed in a position perpendicular to and in fluid communication with the upper portion 22. The upper portion 22 has a proximal end 26 and a distal end 28. The upper portion 22 has a safety cap 30 disposed on the distal end 28. The lower portion 24 has a bottom end 32 and a top end 34.

A direct flow valve 40 is disposed on and in fluid communication with the proximal end 26 of the T-shaped adapter 29 upper portion 22. The direct flow valve 40 has an open position and an alternate closed position.

Figure 2:
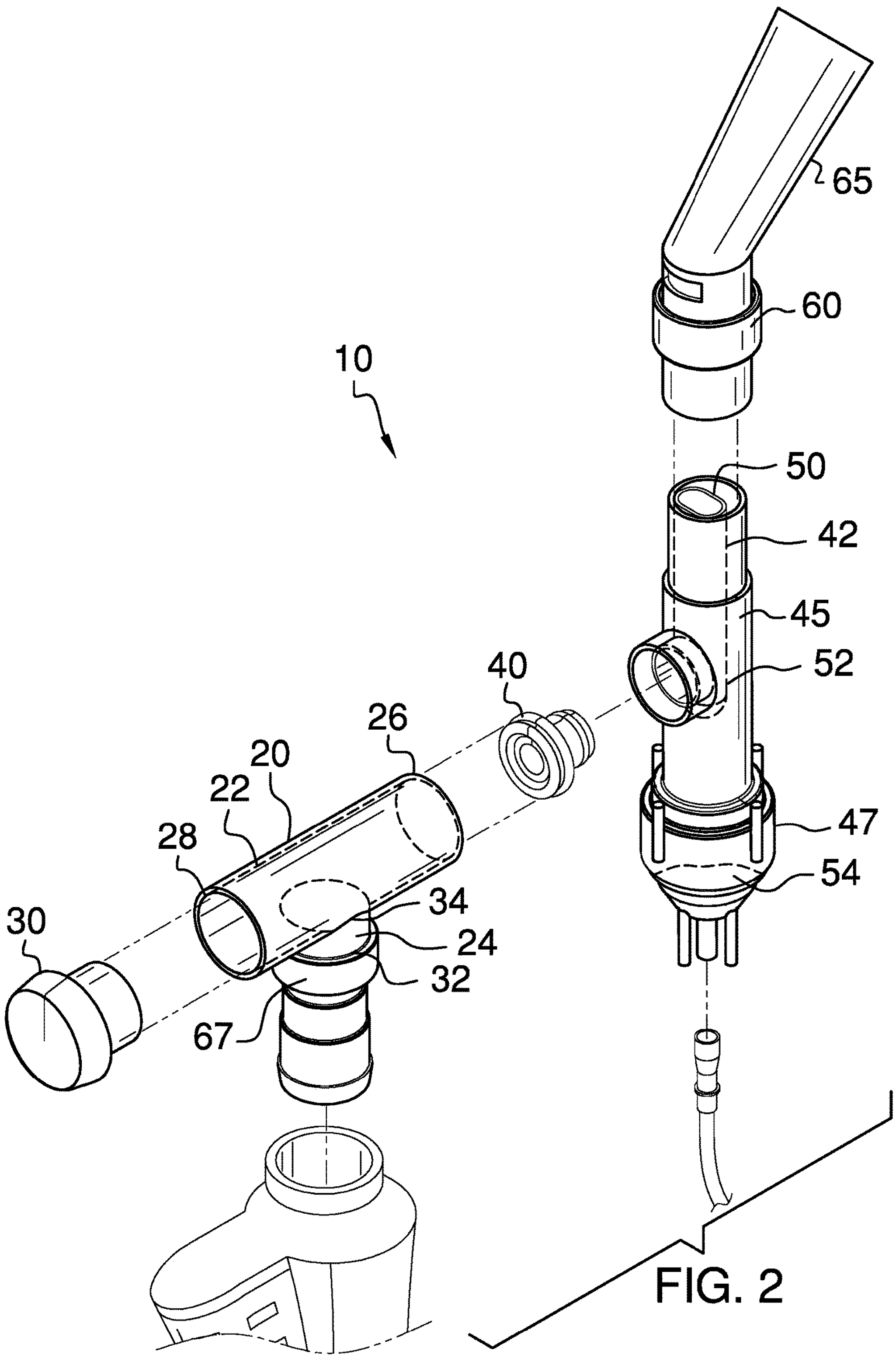
FIG. 2 is an exploded view.
Figure 3:
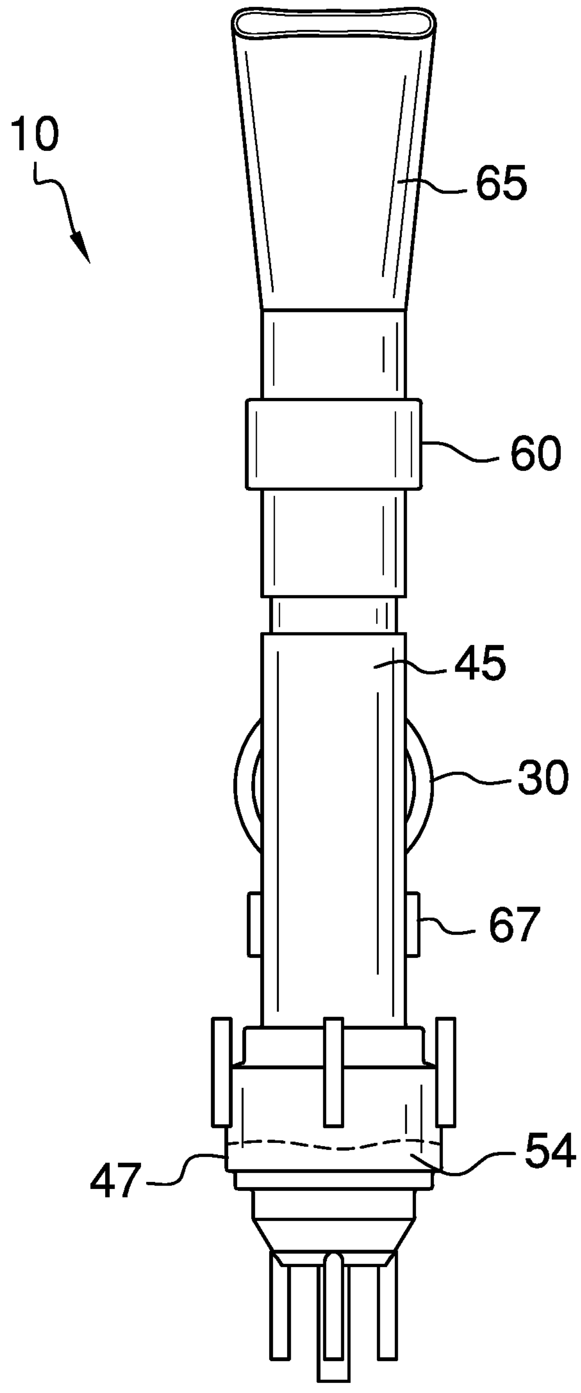
FIG. 3 is a rear elevation view.
Figure 4:
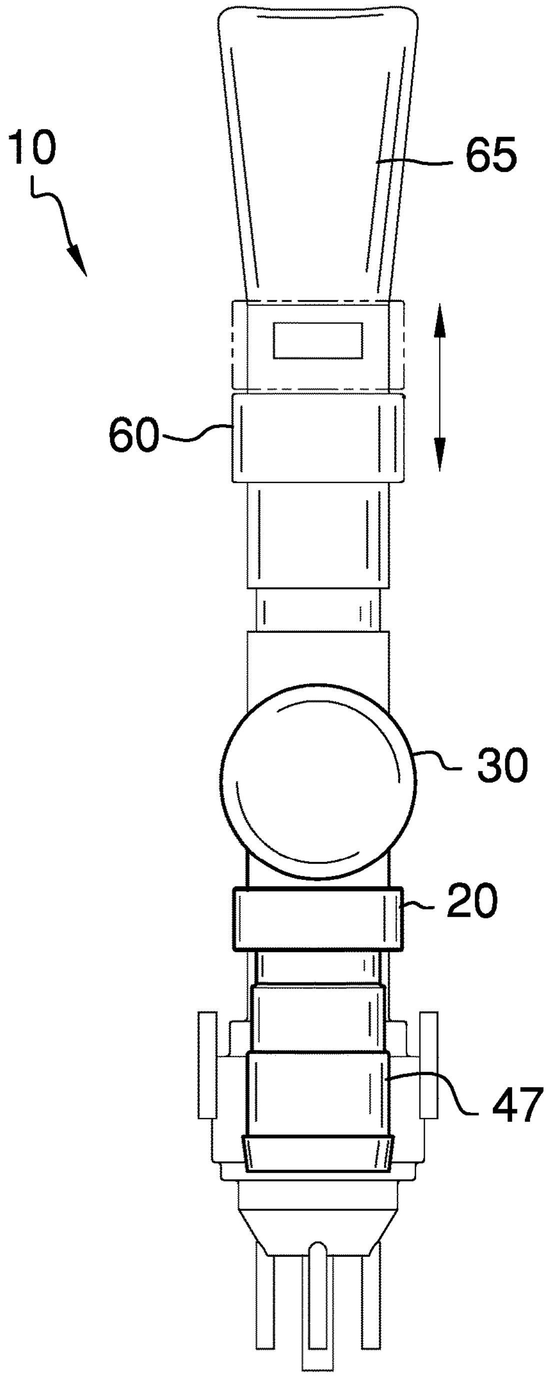
FIG. 4 is a front elevation view.
Figure 5:
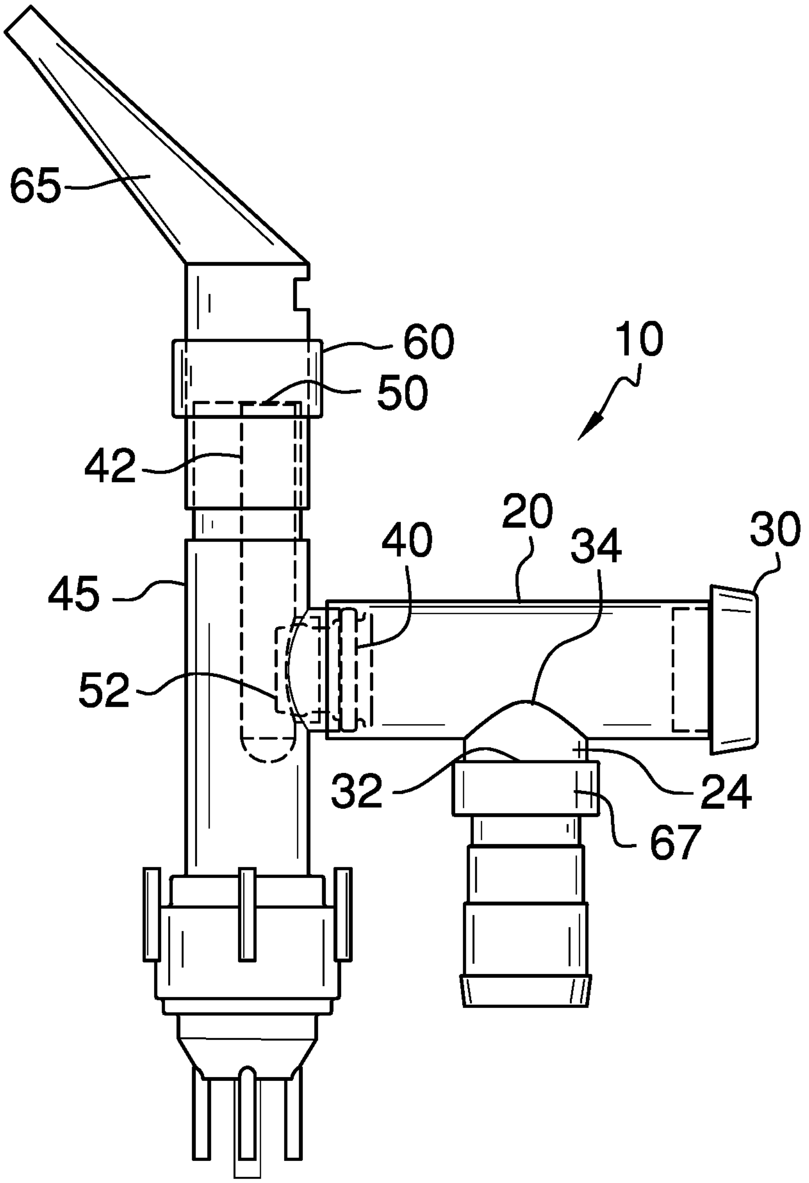
FIG. 5 is a side elevation view.

A direct flow tube 42, shown best in FIG. 2, is disposed within a channel 45 of and in direct fluid communication with a nebulizer medicine reservoir 47. The direct flow tube 42 has an upper end 50 and a lower end 52. The direct flow valve 40 is in operational communication and in fluid communication with the direct flow tube 42 lower end 52. The nebulizer medicine reservoir 47 is a separate body from and in indirect fluid communication with a nebulizer machine 66. An amount of liquid therapy medication 54 is disposed within the nebulizer medicine reservoir 47.

A shut-off valve 60 is disposed between and in fluid communication with the upper end of the direct flow tube 42 and a mouthpiece 65. The shut-off valve 60 has an open position and an alternate closed position. A drip-reduction ring 67 is disposed on the bottom end 32 of the T-shaped adapter 20 lower portion 24. The drip-reduction ring is insertable within an upper outlet of the nebulizer machine. The drip-reduction ring is provided to prevent backflow into the nebulizer machine 66. A gas source 68 is attachable to and configured to be in fluid communication with the nebulizer machine 66.

Upon activation of the nebulizer machine 66, the attachment of the gas source 68 to the nebulizer machine 66, the positioning of the shut-off valve 60 in the open position, the positioning of the direct flow valve 40 in the open position, the gas source is configured to transform the liquid therapy medication 54 disposed within the nebulizer medicine reservoir 47 into a mist. Upon transformation of the liquid therapy medication into a mist, the mist is directed into the direct flow tube 42, through the open shut-off valve 60, and through the mouthpiece 65 for inhalation by the user. The direct flow tube 42, the direct flow valve 40, and the drip-reduction ring 67 operate together to prevent the mist from mixing inside the nebulizer machine 66.

What is claimed is:

1. A nebulizer adapter kit comprising:

a T-shaped adapter having a cylindrical upper portion and a cylindrical lower portion centrally disposed in a position perpendicular to and in fluid communication with the upper portion, the upper portion having a proximal end and a distal end, the lower portion having bottom end and a top end;

a safety cap disposed on the distal end of the upper portion;

a direct flow valve disposed on and in fluid communication with the proximal end of the T-shaped adapter upper portion, the direct flow valve having an open position and an alternate closed position;

a direct flow tube disposed within a channel of and indirect fluid communication with a nebulizer medicine reservoir, the direct flow tube having an upper end and a lower end, the direct flow valve being in operational communication and in fluid communication with the direct flow tube lower end, wherein the nebulizer medicine reservoir is a separate body from and in indirect fluid communication with a nebulizer machine;

an amount of liquid therapy medication disposed within the nebulizer medicine reservoir;

a shut-off valve disposed between and in fluid communication with the upper end of the direct flow tube and a mouthpiece, the shut-off valve having an open position and an alternate closed position;

a drip-reduction ring disposed on the bottom end of the T-shaped adapter lower portion, the drip-reduction ring being insertable within an upper outlet of the nebulizer machine;

wherein a gas source is attachable to and configured to be in fluid communication with the nebulizer machine; and wherein upon activation of the nebulizer machine, the attachment of the gas source to the nebulizer machine, the positioning of the shut-off valve in the open position, the positioning of the direct flow valve in the open position, the gas source is configured to transform the liquid therapy medication disposed within the nebulizer medicine reservoir into a mist, wherein upon transformation of the liquid therapy medication into a mist, the mist is directed into the direct flow tube, through the open shut-off valve, and through the mouthpiece for inhalation by the user.

* * * * *